(12) United States Patent
Pacetti et al.

(10) Patent No.: US 8,414,638 B2
(45) Date of Patent: Apr. 9, 2013

(54) METHOD FOR FABRICATING A POLYMER STENT WITH BREAK-AWAY LINKS FOR ENHANCED STENT RETENTON

(75) Inventors: Stephen D. Pacetti, San Jose, CA (US); Timothy A. Limon, Cupertino, CA (US); Yunbing Wang, Sunnyvale, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 252 days.

(21) Appl. No.: 12/047,040

(22) Filed: Mar. 12, 2008

(65) Prior Publication Data
US 2009/0234432 A1 Sep. 17, 2009

(51) Int. Cl.
*A61F 2/06* (2006.01)

(52) U.S. Cl. ............ 623/1.15; 623/1.11; 623/1.12; 623/1.38

(58) Field of Classification Search .............. 29/418, 29/515, 516, 525.14; 623/1.15, 1.1–1.12
See application file for complete search history.

(56) References Cited

U.S. PATENT DOCUMENTS

| | | | | |
|---|---|---|---|---|
| 5,843,158 A * | 12/1998 | Lenker et al. | .......... | 623/1.13 |
| 6,432,130 B1 * | 8/2002 | Hanson | .......... | 623/1.11 |
| 6,540,777 B2 * | 4/2003 | Stenzel | .......... | 623/1.16 |
| 6,565,599 B1 * | 5/2003 | Hong et al. | .......... | 623/1.15 |
| 6,629,992 B2 * | 10/2003 | Bigus et al. | .......... | 623/1.12 |
| 7,022,132 B2 * | 4/2006 | Kocur | .......... | 623/1.11 |
| 2003/0045923 A1 * | 3/2003 | Bashiri | .......... | 623/1.12 |
| 2003/0114919 A1 * | 6/2003 | McQuiston et al. | .......... | 623/1.15 |
| 2003/0139800 A1 * | 7/2003 | Campbell | .......... | 623/1.15 |
| 2003/0212449 A1 * | 11/2003 | Cox | .......... | 623/1.15 |
| 2004/0127970 A1 * | 7/2004 | Saunders et al. | .......... | 623/1.15 |
| 2005/0273157 A1 * | 12/2005 | Pinchasik | .......... | 623/1.15 |
| 2006/0047336 A1 | 3/2006 | Gale et al. | | |
| 2006/0058863 A1 * | 3/2006 | LaFont et al. | .......... | 623/1.11 |
| 2007/0038290 A1 * | 2/2007 | Huang et al. | .......... | 623/1.16 |
| 2007/0132156 A1 * | 6/2007 | Burgermeister et al. | .......... | 264/479 |
| 2007/0278720 A1 * | 12/2007 | Wang et al. | .......... | 264/430 |
| 2008/0118546 A1 * | 5/2008 | Thatcher et al. | .......... | 424/426 |
| 2008/0206440 A1 * | 8/2008 | Cottone | .......... | 427/2.24 |
| 2011/0270384 A1 * | 11/2011 | Lord | .......... | 623/1.16 |

OTHER PUBLICATIONS

U.S. Appl. No. 10/879,328, Gale et al.
U.S. Appl. No. 11/215,713, Limon et al.
U.S. Appl. No. 11/890,170, Huang et al.

* cited by examiner

*Primary Examiner* — Thomas J Sweet
*Assistant Examiner* — Jacqueline Woznicki
(74) *Attorney, Agent, or Firm* — Squire Sanders (US) LLP (57) ABSTRACT

Polymer stents with break-away links and methods of forming the links for improved stent retention on an expandable member during delivery are disclosed.

2 Claims, 9 Drawing Sheets

METHOD FOR FABRICATING A POLYMER STENT WITH BREAK-AWAY LINKS FOR ENHANCED STENT RETENTON

BACKGROUND OF THE INVENTION

1. Field of the Invention

This invention relates to implantable medical devices, such as stents.

2. Description of the State of the Art

This invention relates to radially expandable endoprostheses, which are adapted to be implanted in a bodily lumen. An "endoprosthesis" corresponds to an artificial device that is placed inside the body. A "lumen" refers to a cavity of a tubular organ such as a blood vessel.

A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a constraining member such as a retractable sheath or a sock. When the stent is in a desired bodily location, the sheath may be withdrawn which allows the stent to self-expand.

The structure of a stent is typically composed of scaffolding that includes a pattern or network of interconnecting structural elements often referred to in the art as struts or bar arms. The scaffolding can be formed from wires, tubes, or sheets of material rolled into a cylindrical shape. The scaffolding is designed so that the stent can be radially compressed (to allow crimping) and radially expanded (to allow deployment). A conventional stent is allowed to expand and contract through movement of individual structural elements of a pattern with respect to each other.

In advancing a stent through a body vessel to a deployment site, the stent must be able to securely maintain its axial as well as rotational position on the delivery catheter without translocating proximally or distally, and especially without becoming separated from the catheter. Stents that are not properly secured or retained to the catheter may slip and either be lost or be deployed in the wrong location. The stent must be "crimped" and retained on the catheter in such a way as to minimize or prevent distortion of the stent and to thereby prevent abrasion and/or reduce trauma to the vessel walls.

Generally, stent crimping is the act of affixing the stent to the delivery catheter or delivery balloon so that it remains affixed to the catheter or balloon until the physician desires to deliver the stent at the treatment site. Current stent crimping technology is sophisticated. Examples of such technology which are known by one of ordinary skill in the art include a roll crimper; a collet crimper; and an iris or sliding-wedge crimper.

Stents can be made of many materials such as metals and polymers, including biodegradable polymer materials. Current intra-arterial stents are composed of a metallic scaffolding or backbone. As such, they are permanent implants. It is the function of a stent to dilate a vessel, tack of dissections, and prevent vasospasm. Once the vessel is fully healed, it is not clear whether the stent serves a further function or purpose. With coronary stents, particularly drug-delivery stents, the complication of thrombosis, both sub-acute, and late is now a serious concern. A completely biodegradable stent may be a solution to the late thrombosis problem as it disappears. Also, in most patients, atherosclerotic disease progresses through life. The biodegradable stent provides patients with additional treatment options for the stented regions.

Thus, biodegradable stents are desirable in many treatment applications in which the presence of a stent in a body may be necessary for a limited period of time until its intended function of, for example, maintaining vascular patency and/or drug delivery is accomplished. A biodegradable polymer stent can be crimped on to a catheter in a manner similar to a metal stent. However, there are problems with stent retention that are unique to polymeric stents.

SUMMARY OF THE INVENTION

Various embodiments of the present invention include a method of fabricating a stent comprising: crimping a polymer stent to a reduced profile, wherein the stent is constructed of a pattern of a plurality of structural elements; and forming at least one breakable connecting element between two structural elements to retain or facilitate retention of the stent at a reduced diameter, wherein the breakable connecting element are capable of breaking to allow expansion of the stent due to a radially outward force on the stent.

Further embodiments of the present invention include a method of fabricating a stent comprising: crimping an axial section of a polymer stent to a reduced profile, wherein the stent is constructed of a pattern of a plurality of structural elements; forming at least one breakable connecting element connecting two structural elements of the axial section; and repeating the crimping and forming steps for an adjacent uncrimped axial section of the stent.

Yet another embodiment of the present invention includes a method of fabricating a stent comprising: crimping the full length of a polymer stent to a reduced profile, wherein the stent is constructed of a pattern of a plurality of structural elements; and forming at least one breakable connecting element connecting two structural elements of the stent within the crimper by application of heat, ultrasonic welding, adhesive bonding or solvent bonding.

Additional embodiments of the present invention include a method of fabricating a stent comprising: disposing a stent-catheter assembly at an implant site within a vascular lumen, the stent crimped to a reduced profile over the catheter, the stent comprising at least one breakable connecting element between two structural elements for retaining or facilitating retention of the stent at reduced diameter prior to implanting the stent; and applying a radially outward force to radially expand the stent, the force breaking the connecting elements to allow the expansion of the stent at the implant site.

Other embodiments of the present invention include a stent comprising: a pattern formed of a plurality of polymeric structural elements; and at least one breakable connecting element connecting two structural elements, the connecting element retaining or facilitating retention of the stent at a reduced diameter prior to implanting the stent, wherein the breakable connecting elements are capable of breaking to allow expansion of the stent due to a radially outward force on the stent during implantation of the stent.

DETAILED DESCRIPTION OF THE INVENTION

Embodiments of the present invention relate to facilitating retention of polymeric stents on a delivery catheter for delivery of a stent at an implant site in a vascular lumen. These embodiments also apply to stent-grafts and generally tubular medical devices.

In some embodiments, embodiments of the present invention are particularly directed to retention of biodegradable, polymeric stents on a balloon of a catheter assembly. A biodegradable polymer stent has many advantages over metal stents, including the ability to be placed in the body only for the duration of time until the intended function of the stent has been performed.

However, retention of a polymer stent on a delivery catheter has been proven to be more challenging than that of a metallic stent. Polymeric materials, in general, have lower yield stress and higher elastic strain than metals. This results in the polymeric stent gripping the balloon with less force after crimping. Polymer stents can require wider struts than metal stents so as to provide suitable mechanical properties, such as material strength, for the stent. At the crimping stage, less space is provided between the struts which can result in worse stent retention than a metallic stent. Moreover, the use of high processing temperature during the crimping process to enhance stent retention may not be possible since a polymeric stent may have a glass transition temperature (Tg) close to body temperature. Higher processing temperatures may cause the polymeric stent to lose some of its preferred mechanical properties.

In certain embodiments, a stent is a tubular device constructed of a pattern of a plurality of interconnected structural elements which are often also referred to as struts or bar arms. In such embodiments, a stent can include circumferential rings connected by linking struts.

Figure 1:
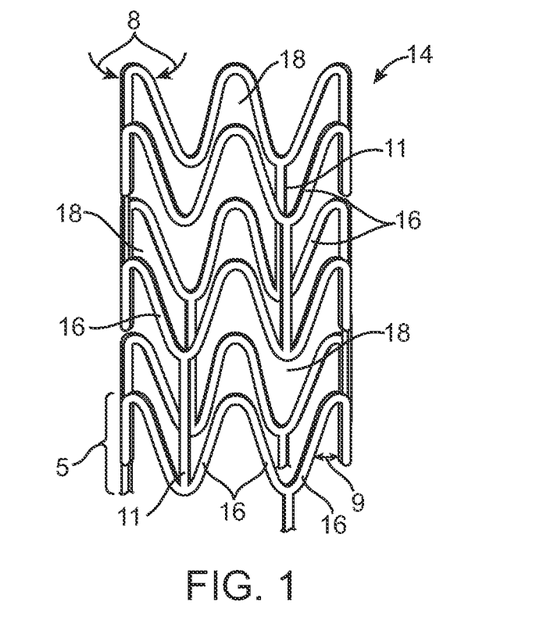
FIG. 1 depicts a stent.

Referring to FIG. 1, an exemplary stent 14 is illustrated. Stent 14 can include a plurality of structural elements or struts 16 connected by linking struts 11, with interstitial spaces 18 located in between the struts. The plurality of struts 16 can be configured in an annular fashion in discrete "rows" such that they form a series of "circumferential rings 5" throughout the body of stent 14.

A stent pattern such as that pictured in FIG. 1 is configured to be radially compressible and expandable to allow the stent to be crimped to reduced profile during delivery and deployed at an implant site, respectively. A stent can be positioned over a delivery catheter and compressed or crimped to a delivery diameter. "Delivery diameter" refers to a diameter at which a stent is introduced and transported in a bodily lumen. The bending of the structural elements of a stent pattern allow it to contract as the stent is crimped or expanded as the stent is deployed. For example, structural elements of stent 14 can bend inward to allow crimping as shown by arrows 8 and outward as shown by arrow 9.

Figure 2A:
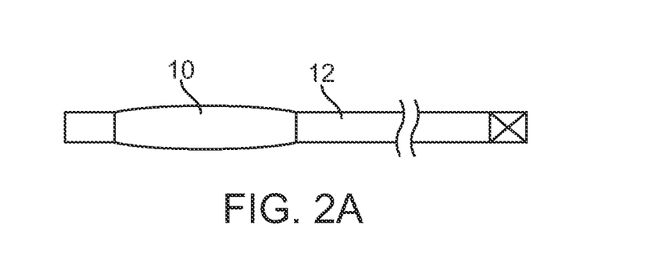
FIG. 2A depicts an expandable member.
Figure 2B:
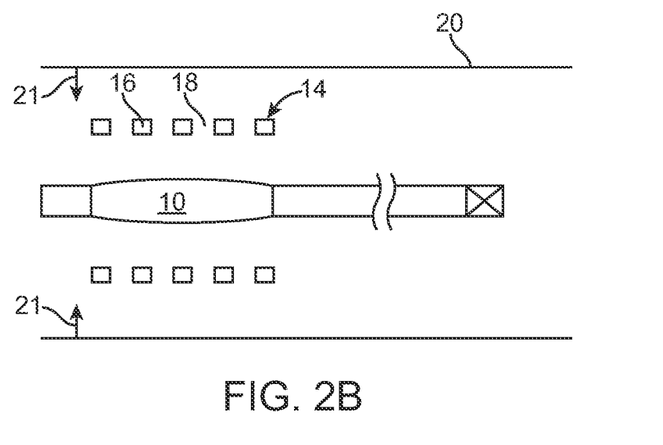
FIGS. 2B-C illustrate a crimping process of a stent onto an expandable member.
Figure 2C:
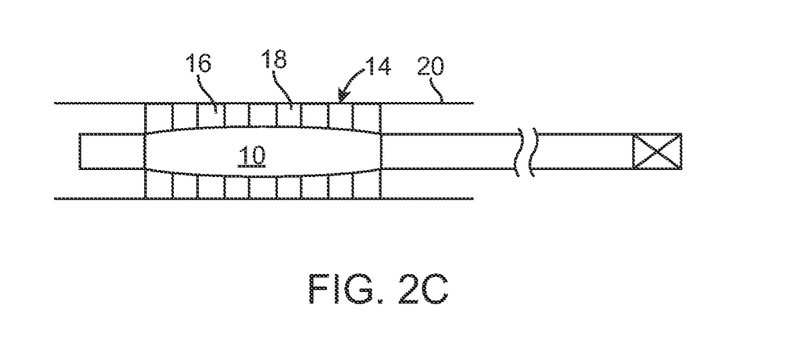

FIGS. 2A-C illustrate the crimping process. FIG. 2A depicts an expandable member, such as a balloon 10, integrated at a distal end of a catheter assembly 12. In some embodiments, balloon 10 is intended to include any type of enclosed member such as an elastic type member that is selectively inflatable to dilate from a collapsed configuration to a desired and controlled expanded configuration. The balloon 10 should also be capable of being deflated to a reduced profile or back to its original collapsed configuration. FIG. 2B illustrates a stent 14 in cross section positioned over balloon 10. Stent 14 is illustrated to have struts 16 separated by gaps 18 (as can also be seen in FIG. 1). In some embodiments, the diameter of stent 14 as positioned over the collapsed balloon 10 is much larger than the collapsed diameter of the balloon 10.

Additionally, as illustrated in FIG. 2B, the balloon 10 and the stent 14 are positioned in a crimping device 20. Stent 14 can be positioned in device 20 and held in place by application of pressure from crimping device 20. The device may also optionally heat the stent during crimping. The crimping device 20 can be any device used in the art or in this disclosed herein. Crimping device 20 then applies inward radial pressure to the stent 14 on the balloon 10, as shown by arrows 21. Stent 14 positioned over the balloon 10 is crimped to a reduced stent configuration (reduced crimped configuration), as illustrated in FIG. 2C.

Figure 2D:
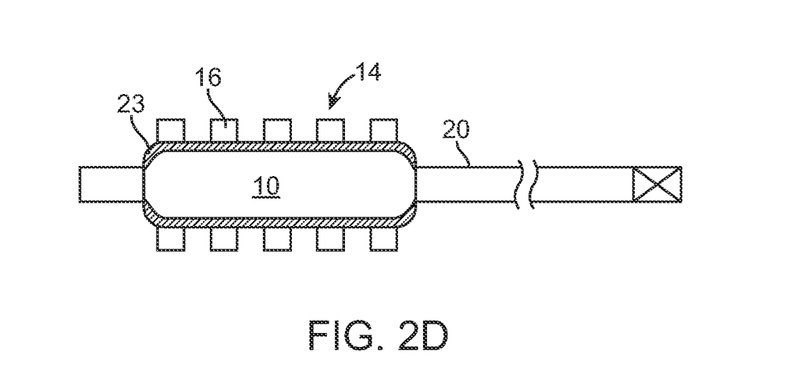
FIG. 2D depicts a stent expanded or deployed due to inflation of a balloon.

FIG. 2D depicts stent 14 expanded or deployed due to inflation of balloon 10. An inflation fluid such as a gas or liquid is pumped into the balloon to inflate it. The radially outward force from the inflated balloon expands the stent to a delivery diameter.

As the structural elements bend, they plastically deform which results in a gripping force on the catheter by the stent. Metal stents deform plastically with a relatively small strain to yield which facilitates stent retention. However, polymers have a lower flexural and tensile moduli than metals and have relatively larger strains to yield than metals. As a result, the gripping force of polymer stent is lower than a metal stent. In addition, polymer stents are susceptible to creep which can also reduce stent retention. Stents can be exposed to elevated temperatures during sterilization, either from methods based on radiation or ethylene oxide, which further increases creep. If the gripping force is not sufficient, a stent may have a tendency to shift position or separate from the catheter prior to delivery.

Embodiments of the present invention include connecting, linking, or fusing structural elements to facilitate retention of a stent on a catheter. In such embodiments, breakable linking connecting elements are employed to facilitate retention of a polymeric stent on a delivery catheter. These breakable linking elements maintain a stress, gripping the balloon, that would not be present in a crimped stent pattern without breakable links. In these embodiments, a stent is crimped to a reduced profile over a support element or catheter and a portion of the structural elements are connected, linked, or fused. At least one breakable connecting element is formed that connects or links two structural elements to retain or facilitate retention of the stent on a support element such as a delivery catheter or balloon. The breakable connecting element(s) retain or facilitate retention of the stent at the crimped diameter and on the support element.

As described below, portions of structural elements can be connected or linked through formation of connecting elements using various methods including thermal welding, solvent welding, laser welding, application of polymer solution, application of adhesives, or ultrasonic welding. In these embodiments, the stent may be crimped to a reduced profile so that the portions of structural elements to be joined are in contact or close enough to allow linking and forming the connecting elements between such portions.

As indicated above, a stent contracts and expands through movement of structural elements with respect to one another. In these embodiments, parts, portions, or sections of structural elements that tend to move apart upon expansion of the stent are fused or connected, thus reducing or preventing expansion. The movement that is reduced or prevented can be circumferential or longitudinal. For example, the movement of structural elements depicted by arrows 8 and 9 of FIG. 1 is roughly circumferential.

Embodiments of the present invention can including forming connections between portions of any such structural elements that are in contact or closely spaced upon crimping the stent. The connecting elements formed between such structural elements reduce or prevent movement of such structural elements with respect to one another, thus retaining the stent at the crimped configuration.

In some embodiments, connecting elements are formed between structural elements on neighboring cylindrical rings that tend to move apart to allow expansion of a stent from a crimped profile. In other embodiments, portions of structural elements can be connected that bend inward to allow crimping or outward to allow expansion, as shown by arrows 8 and arrow 9 of FIG. 1, respectively.

Figure 3A:
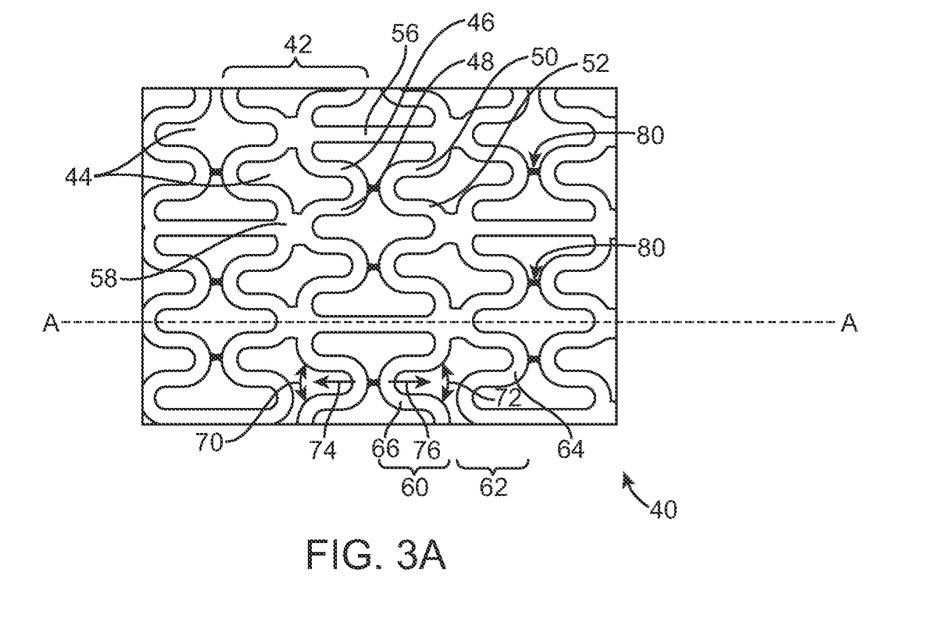
FIG. 3A depicts a stent pattern shown in a flattened condition.

FIG. 3A depicts a stent pattern 40 shown in a flattened condition so that the pattern can be clearly viewed. When the flattened portion of stent pattern 40 is in a cylindrical form, it forms a radially expandable stent. Stent pattern 40 includes a plurality of cylindrical rings 42 of diamonds with each ring including a plurality of diamond-shaped cells 44. Embodiments of stent pattern 40 may have any number of rings 42 depending on the desired stent length. For reference, line A-A represents the longitudinal axis of a stent using the pattern depicted in FIG. 3A. Diamond shaped cells 44 are made up of struts 46 and 48 that form a curved element and struts 50 and 52 that form an opposing curved element.

Pattern 40 further includes linking struts 56 that connect adjacent cylindrical rings. Linking struts 56 are parallel to line A-A and connect adjacent rings between intersections 58 of cylindrically adjacent diamond-shaped elements 44 of one ring and intersection 58 of cylindrically adjacent diamond shaped elements 44 of an adjacent ring. As shown, linking elements connect every other intersection along the circumference. Rings 42 can also be described as being formed by two opposing undulating rings 60 and 62 with opposing peaks 64 and 66.

As shown in FIG. 3A, stent pattern 40 is in a crimped or reduced profile state. Radial expansion from the reduced profile state is allowed through the outward bending of the curved elements formed by struts 46 and 48 and struts 50 and 52, as shown by arrows 70 and 72. As the curved elements bend, they move apart as shown by arrows 74 and 76.

As shown in FIG. 3A, curved elements on adjacent rings are connected or fused. Stent pattern 40 has connecting elements 80 that connect the peaks of the curved elements formed by struts 46 and 48 and struts 50 and 52. Connecting elements 80 prevent the curved elements from moving away and bending. Connecting elements 80 reduce or prevent radial expansion of stent pattern 40 and are under tension due to a tendency for stent pattern 40 is expand. The tension of connecting elements 80 results in a radially directed gripping force that facilitates retention of the stent on a supporting element.

The connecting elements can be selectively distributed throughout the pattern to achieve a desired retention of the stent on the supporting element. In one embodiment shown in FIG. 3A, connecting elements connect all of the peaks of adjacent of adjacent rings around a circumference of the stent. In other embodiments, the connecting elements connect some, but not all of the peaks of adjacent rings around a circumference of a stent. For example, alternating peaks of adjacent rings may be connected.

Figure 3B:
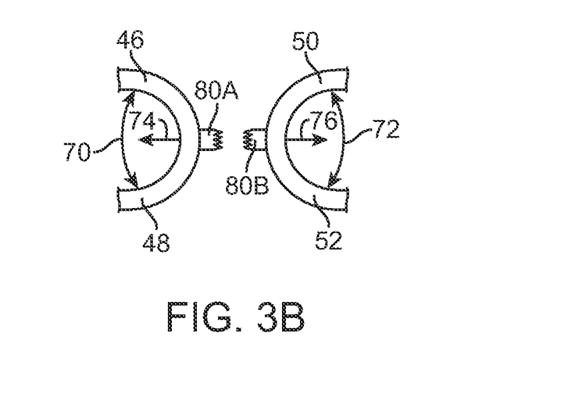
FIG. 3B depicts a close-up view of a curved structural element of a stent.

In these embodiments, the connecting elements are capable of breaking to allow expansion of the stent during stent implantation. In such embodiments, the stent can be mounted over an expandable member which applies a radially outward force. The force is high enough to cause the connecting elements to fracture, split, or break to allow expansion of the stent. FIG. 3B depicts a close-up view of a curved element as it expands due to the outward radial force from an expandable member. The curved elements defined by struts 46 and 48 and struts 50 and 52 bend outward as shown by arrows 70 and 72. The outward radial force is strong enough to break connecting element 80 to allow the expansion, forming pieces 80A and 80B. In other embodiments, a connecting element can break off of one of the curved elements leaving the entire connecting element on one of the curved elements. In additional embodiments, the connecting element can break off of both of the curved elements. However, generation of particulates is generally undesirable as they can constitute an embolic hazard. Consequently, the connecting element can be designed so that it parts in a specified location without shedding any particles.

Figure 4A:
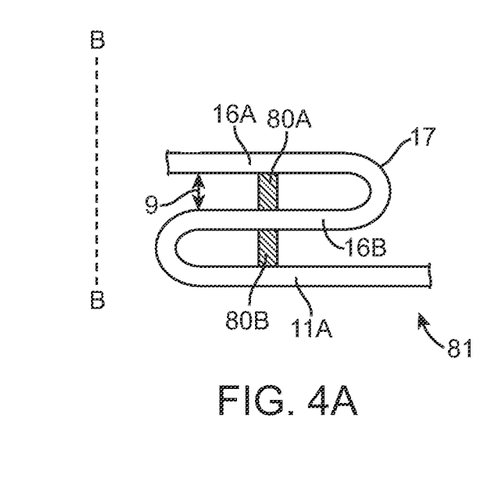
FIGS. 4A-B depict connected structural elements.

Another exemplary embodiment is shown in FIG. 4A which depicts a section 81 of stent 14 of FIG. 1 in a crimped state. FIG. 4A depicts a bending element 17 made up of struts 16A and 16B which move apart as shown by arrow 9. Line B-B represents the circumferential direction of stent 14. Struts 16A and 16B are connected by a connecting element 80A which reduces or prevents outward bending of bending element 17. Additionally, struts 16B and 11A are connected by a connecting element 80B which reduces or prevent outward bending of struts 16B and 11A. Such connecting elements can be distributed throughout the stent pattern of stent 14 to reduce or prevent expansion of the stent from the crimped state.

Figure 4B:
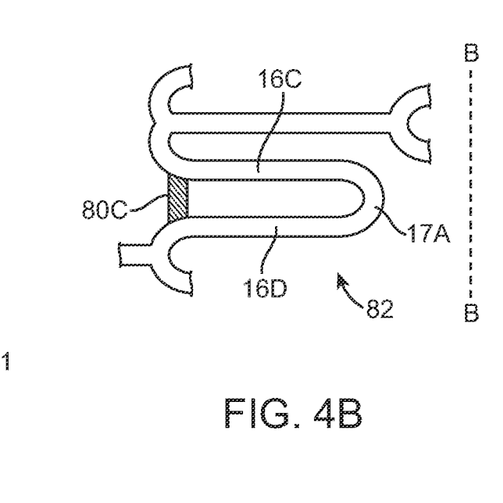

FIG. 4B depicts another exemplary embodiment depicting a section 82 of stent 14 of FIG. 1 in a crimped state. FIG. 4B depicts a bending element 17A made up of struts 16C and 16D which move apart. Line B-B represents the circumferential direction of stent 14. Struts 16C and 16D are connected by a connecting element 80C which reduces or prevents outward bending of bending element 17.

Figure 5A:
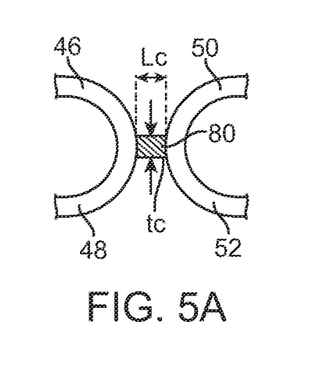
FIGS. 5A-C depict connected structural elements.
Figure 5B:
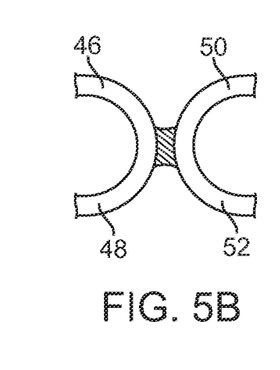
Figure 5C:
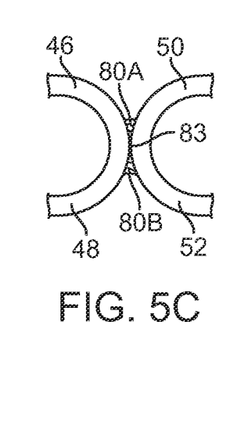

In certain embodiments, the dimensions or mass of connecting elements or links can be adjusted to allow breaking of the links upon application of a radial force on the stent by an expandable member. A pressure applied by an expandable member can be in the range of 2 to 16 atm. For example, a thickness or average thickness, tc, of connecting element 80 in FIG. 5A can be adjusted. Increasing to increases both the mass of the connecting elements and the surface area of the portions of the structural elements that are fused or connected, thus increasing the strength of the connection. Additionally, a ratio of a length, lc, of the connecting elements to tc can be one, greater than one (FIG. 5A), or less than one (FIG. 5B). In some embodiments, connecting elements can be separated by a point or region of contact between connected structural elements. FIG. 5C illustrates a point of contact 83 between connecting elements 80A and 80B.

In some embodiments, structural elements can be connected or fused by thermal welding, or more generally, by applying heat to soften or melt polymer material of the structural element or a bonding or connecting polymer. In such embodiments, portions of structural elements can be heated to soften or melt the portions of structural elements to be connected. In one embodiment, the portions are in contact and upon cooling, the portions are connected or fused. In another embodiment, the softened or melted portions are closely spaced. The closely-spaced softened or melted portions can be then be brought into contact by further radial compression of the stent. Upon cooling the portions are fused or connected. In an additional embodiment, upon softening or melting, a bridge of polymer material is formed between the portions and upon cooling the portions are connected or fused. In further embodiments, a melted polymer material can be disposed between contacted or closely spaced portions of the structural element and allowed to cool to connect or fuse the structural elements.

In another embodiment, a melted polymer composition can be applied between or on the portions of the structural elements to be joined to form the connecting element. The polymer composition can be the same or different from the polymer material that makes up the structural elements. In one embodiment, formation of the connecting element from the polymer composition does not melt polymer material of the structural elements. The melted material adheres to the structural elements and solidifies to form the connecting elements. In one embodiment, the melting temperature (Tm) of the connecting element composition is less than the polymer composition of the coating on the structural element, the scaffolding polymer of the structural element, or both.

In certain embodiments, a connecting element polymer material can be selected to have different mechanical properties from the scaffolding polymer of the structural elements. In particular, a material for the connecting element can be selected that has a propensity to fracture or break when a radial force is applied the stent during deployment. In one embodiment, the connecting element polymer material is a brittle or glassy polymer at human body temperature, which is approximately 37° C. Such a material has a Tg above human body temperature. In some embodiments, the connecting element polymer has a lower strength, lower elongation at break, or both than the scaffolding polymer. In exemplary embodiments, a connecting element polymer includes poly(L-lactide) (PLLA), poly(L-lactide-co-D,L-lactide), poly(D,L-lactide), poly(D,L-lactide-co-glycolide), poly(glycolide) and poly(L-lactide-co-glycolide) (PLGA).

In some embodiments, the connecting element may be composed of biodegradable or biosoluble material. The connecting element may also be composed of a bioabsorbable metal or metallic alloy. The connecting element may be exposed to bodily fluid during delivery prior to deployment, resulting in degradation of the mechanical properties of the connecting element. The degradation in mechanical properties can facilitate the breaking of the connecting element upon deployment of the stent. In such embodiments, the connecting element material can have a higher degradation rate than the polymer of the structural element to further facilitate the breaking of the connecting element upon deployment. In an exemplary embodiment, the scaffolding of the stent can be formed from PLLA and the connecting element material can be a faster degrading material such as polyglycolide (PGA) or PLGA.

Figure 6A:
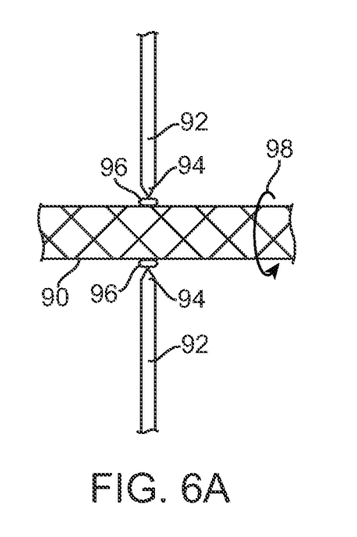
FIG. 6A depicts a schematic illustration of a stent in a crimped state.

In certain embodiments, heat can be applied to fuse or connect portions of structural elements with a heating element, such as a heated metal tip. FIG. 6A depicts a schematic illustration of a stent 90 in a crimped state. Heating elements 92 with heated tips 94 are positioned adjacent or in contact with structural elements to be joined. A polymer composition 96 is shown melted by heated tips 94. Stent 90 can be disposed over a rotatable support which allows rotation of stent 90, as shown by an arrow 98 so that connecting elements can be formed around at selected locations around the circumference of stent 90.

Figure 6B:
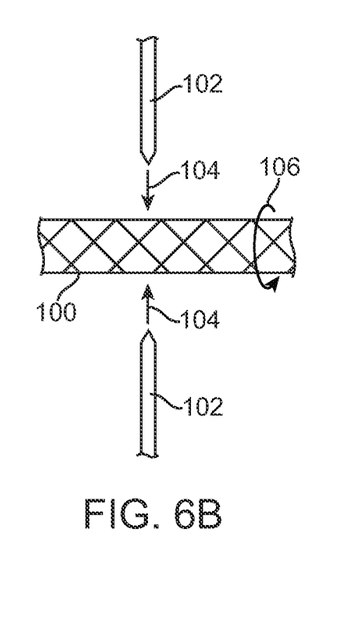
FIG. 6B depicts a schematic illustration of a stent in a crimped state.

In additional embodiments, laser energy can be used to form connecting elements between structural elements. In such embodiments, laser energy can be focused on structural elements to be joined to melt the structural elements to form a connecting element. Exemplary lasers include excimer, ultraviolet, infra-red, visible and ultra-fast pulse lasers. Infra-red lasers heat polymeric materials effectively although ultraviolet and excimer lasers can work as well. FIG. 6B depicts a schematic illustration of a stent 100 in a crimped state. Laser beam sources 102 are positioned to direct laser energy onto closely spaced structural elements or structural elements in contact. Laser energy is directed as shown by arrows 104 to melt a portion of structural elements to form connecting elements between them. In other embodiments, a connecting element polymer composition is positioned adjacent the structural elements and melted with laser energy to form connecting elements. As shown in FIG. 6B, stent 100 can be rotated, as shown by an arrow 106 so that connecting elements can be formed at selected locations around the circumference of stent 100.

In further embodiments, structural elements can be connected or fused through the use of solvent bonding. In general, solvent bonding refers to the process of joining structural elements made of polymers by applying a solvent capable of dissolving, swelling, or softening the surfaces to be joined, and contacting the surfaces treated by the solvent. Upon removal of the solvent through evaporation, the surfaces are fused or connected. In these embodiments, a solvent can be applied to closely spaced or structural elements in contact. The solvent is capable of dissolving or swelling the polymer of the scaffolding. Representative examples of solvents may include, but are not limited to, chloroform, acetone, tetrahydrofuran, chlorobenzene, ethyl acetate, 1,4-dioxane, ethylene dichloride, 2-ethyhexanol, and combinations thereof.

Figure 7A:
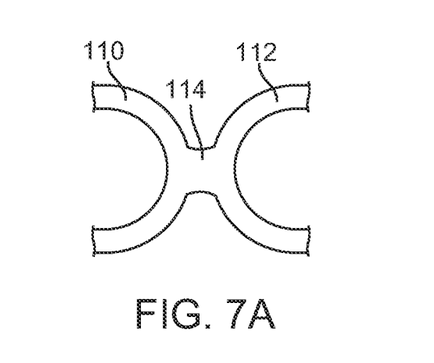
FIG. 7A depicts structural elements treated with a solvent to form a solvent bridge between the structural elements.
Figure 7B:
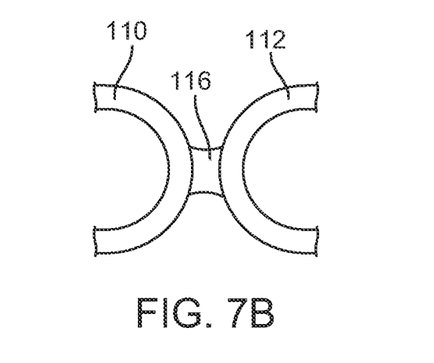
FIG. 7B depicts the structural elements of FIG. 7A with a connecting element or link formed between the structural elements.

In some embodiments, an amount of solvent is applied to closely spaced portions of structural elements to form a connection or bridge of a polymer solution between the structural elements. The solution includes dissolved polymer from the structural element. The solvent from the solution may then be removed through evaporation, leaving a connecting element composed of the polymer of the structural element. FIG. 7A depicts structural elements 110 and 112 that have been treated with a solvent that has formed a bridge 114 between the structural elements. As shown in FIG. 7B, upon removal of the solvent, a connecting element 116, is formed between structural elements 110 and 112. The solvent can be applied by various methods such as by means of a micro-syringe, injet type nozzle, or piezoelectric dispenser. The solvent can be allowed to evaporate at room temperature. Alternatively, a room temperature or heated gas can be blown on the stent to facilitate evaporation of the solvent.

In another embodiment, solvent is applied to portions of the structural elements to be connected to form a polymer solution on a surface of the treated portions. The treated portions are then brought in to contact, for example, by additional radial compression or crimping of the stent. Removal of the solvent results in the formation of a connecting element between the structural elements made from the polymer of the structural element.

In additional embodiments, a connecting element between structural elements may be formed using a polymer solution containing a polymer which is the same or different from a polymer of the structural element. The polymer solution may be applied in a manner similar to that described in solvent bonding. For instance, a polymer solution may be applied to a surface of closely spaced structural elements. In one embodiment, a bridge of solution is formed between the structural elements. Alternatively or additionally, the treated portions of the structural elements can be brought into contact, for example, by further crimping or radial compression of the stent. The solvent in the solution may then be removed from the solution as discussed above, leaving a connecting element composed of the polymer in the solution. In some embodiments, the polymer in the solution is different from the polymer of the structural element and the solvent of the solution may be a nonsolvent or weak solvent for the polymers of the structural element.

In further embodiments, various types of biostable and biodegradable adhesives may be used to form connecting elements. Exemplary adhesives include, but are not limited to, thermosets such as, for example, epoxies, polyesters and phenolics; thermoplastics such as, for example, polyamides, cyanoacrylates, polyesters and ethyl vinyl acetate (EVA) copolymers; and elastomers such as, for example, natural rubber, styrene-isoprene-styrene block copolymers, and polyisobutylene. Other adhesives include, but are not limited to, proteins; cellulose; albumin; starch; poly(ethylene glycol); fibrin glue; and derivatives and combinations thereof.

Various methods may be used to selectively apply materials discussed in the above embodiments to a stent, i.e., polymer melts, solvents, polymer solutions, and adhesives. Such methods include ink-jet-type coating, electrostatic coating, roll coating, thermal deposition with masking, plasma polymerization with masking, direct application of polymer/solvent solution by micro-syringe, direct polymer melt application, and spray coating with photomasking. In an exemplary embodiment, a controlled deposition system ink-jet-type coating method can be used that applies various substances only to certain targeted portions of a stent. A representative example of such a system, and a method of using the same, is described in U.S. Pat. No. 6,395,326 to Castro et al. A controlled deposition system can be capable of depositing a substance on a stent having a complex geometry, and otherwise apply the substance so that substance is limited to particular portions of the stent, such surfaces of structural elements that are to be joined or connected. The system can have a dispenser and a holder that supports the stent. The dispenser and/or holder can be capable of moving in very small intervals, for example, less than about 0.001 inch. Furthermore, the dispenser and/or holder can be capable of moving in the x-, y-, or z-direction, and be capable of rotating about a single point.

The controlled deposition system can include a dispenser assembly. The dispenser assembly can be a simple device including a reservoir, which holds a substance such as a polymer melt, solvent, polymer solution, adhesive, prior to delivery, and a nozzle having an orifice through which the substance is delivered. One exemplary type of dispenser assembly can be an assembly that includes an ink-jet-type printhead. Another exemplary type of a dispenser assembly can be a microinjector capable of injecting small volumes ranging from about 2 to about 70 nL, such as NanoLiter 2000 available from World Precision Instruments or Pneumatic PicoPumps PV830 with Micropipette available from Cell Technology System. Such microinjection syringes may be employed in conjunction with a microscope of suitable design.

Furthermore, selective application of substances to surfaces of a stent may be performed using photomasking techniques. Deposition and removal of a mask can be used to selectively apply substances to surfaces of substrates. Masking deposition is known to one having ordinary skill in the art.

Additionally, the substances of the present invention can also be selectively deposited by an electrostatic deposition process. Such a process can produce an electrically charged or ionized substance. The electric charge causes the substance to be differentially attracted to the stent, thereby resulting in higher transfer efficiency. The electrically charged substance can be deposited onto selected regions of the stent by causing different regions of the device to have different electrical potentials.

In further embodiments, ultrasonic welding may be used to connect or fuse structural elements. Ultrasonic welding refers to a technique in which high-frequency ultrasonic acoustic vibrations are used to weld objects together, typically plastics. In ultrasonic welding an element for emitting ultrasonic vibrations, a sonotrode or horn is connected to a transducer. The sonotrode is positioned against the portions to be welded and a very rapid (~20,000 KHz), low-amplitude acoustic vibration is applied to the portions. Typically, in ultrasonic welding, the portions to be welded are sandwiched between an ultrasonic transducer and a rigid support. The transducer and support may be configured as pincers to clamp the positions together before applying the ultrasonic energy. The acoustic energy is converted into heat by friction so that portions to be welded are ultimately connected or fused by the heat generated.

As discussed above, fusing, bonding, or forming a connection between portions of structural elements using the methods described above requires the stent to be in a sufficiently reduced profile or crimped state so that such portions to be sufficiently close or in contact. In some embodiments, the connecting elements are formed after crimping in the absence a radial compressive force. In such embodiments, the portions of the structural elements are close enough or in contact that to allow formation of the connecting elements. The stent can be removed from the crimper and then one of the above techniques is applied to form the connecting elements.

In other embodiments, sufficiently close spacing or contact of the portions of the structural element may require inward radial compression during the fusing or connecting process. In some embodiments, the connecting elements can be formed during crimping. In one such embodiment, an axial section of a stent is crimped to a reduced profile and a connection is formed between structural elements of the axial section. In an exemplary embodiment, an axial segment of a stent can be disposed in a short bore crimper. The crimper reduces the profile of axial segment within the bore and an axial portion extending out from the proximal side of the bore. One or more connections may be formed between structural elements in the axial portion extending out from the proximal side of the crimper bore. An uncrimped axial segment proximal to the crimped section is then positioned within the crimper bore. The axial segment is crimped, followed by the formation of connections to structural elements, as described above. The process is repeated in a step-wise fashion until the entire length of the stent is crimped and connections formed along the its length.

Figure 8A:
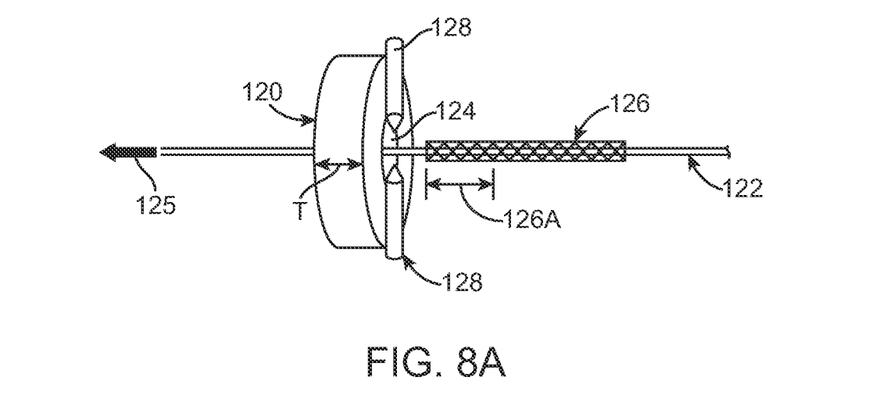
FIG. 8A illustrates crimping and formation of connections between structural elements in a step-wise fashion.

FIG. 8A illustrates crimping and formation of connections between structural elements in a step-wise fashion. FIG. 8A depicts a short bore crimper 120 and a catheter 122 positioned through a bore 124 of short bore crimper 120. An axial thickness T of short bore thickness is not long enough to crimp an entire axial length of a stent 126 disposed over catheter 122 and positioned just outside of bore 124. To crimp an axial segment 126A of stent 126, it is positioned within bore 124 in the direction of an arrow 125 followed by radial compression of the axial segment. Laser beam sources 128 are positioned to direct laser energy onto a crimped portion of stent 126 to form connections between structural elements.

Figure 8B:
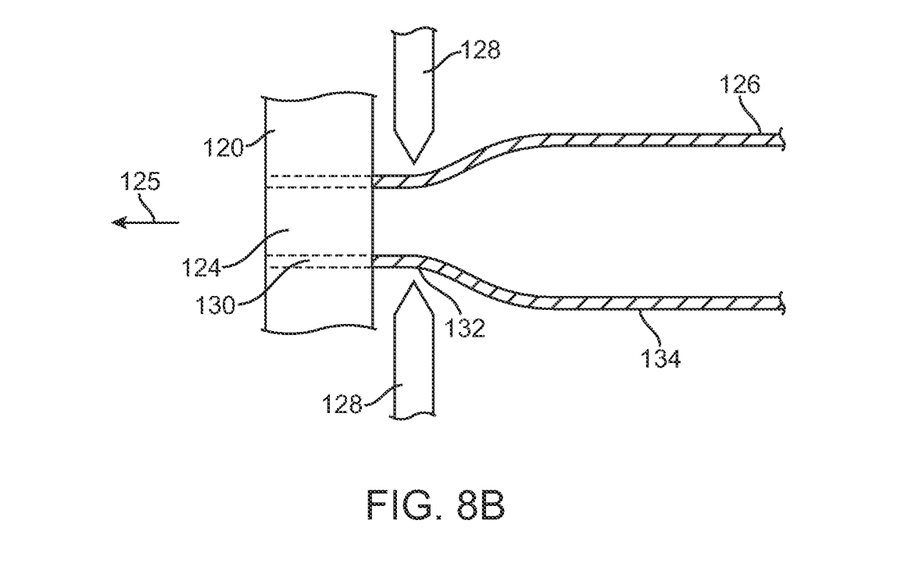
FIG. 8B depicts a close-up view of an axial section of a stent positioned within a bore of a crimper and crimped to a reduced profile.

FIG. 8B depicts a close-up view of an axial section 130 of stent 126 positioned within bore 124 and crimped to a reduced profile. A proximal axial section 132 extending out of bore 124 also has a reduced profile and axial section 134 is uncrimped. Laser beam sources 128 are then used to form connections between structural elements in axial section 132. The method of forming the connections is not limited to laser welding. For example, a heated tip, an ultrasonic welder, or a dispenser for dispensing solvent, polymer solution, polymer melt, or adhesive can be used. After crimping and forming the connections, the stent is moved axially in the direction of arrow 125 and another axial section is crimped followed by formation of connections between structural elements.

Figure 8C:
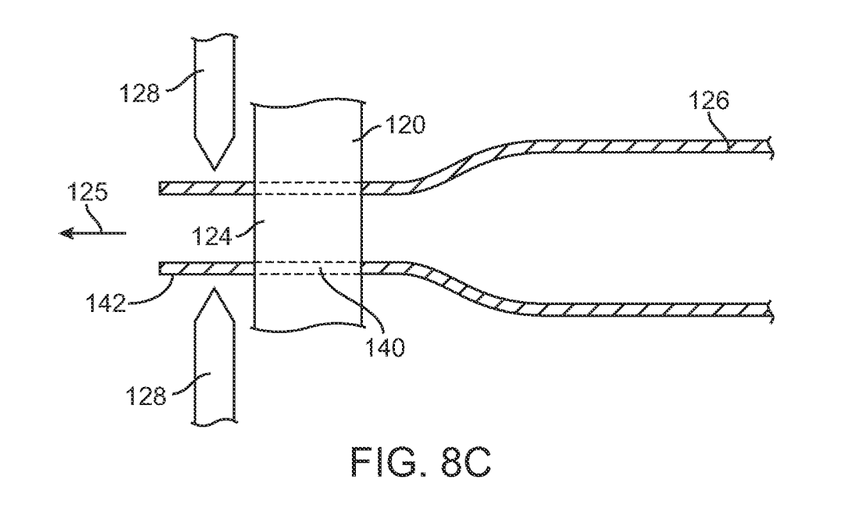
FIG. 8C depicts a close-up view of the stent of FIGS. 8A-B with a crimped axial section within the bore of the crimper.

In an alternate embodiment, connections between structural elements can be formed in a crimped axial section of a stent extending out from distal side of a crimper bore. FIG. 8C depicts a close-up view of stent 126 with a crimped axial section 140 within bore 124 of crimper 120. A crimped proximal axial section 142 extends out of the distal side of bore 124. Axial section 142 has already been crimped by crimper 120. Laser beam sources 128 are positioned on the distal side of bore 124 to form connections between structural elements in axial section 142. Stent 126 is crimped and connections are formed in a step-wise fashion until the entire length of stent 126 is crimped.

Figure 9:
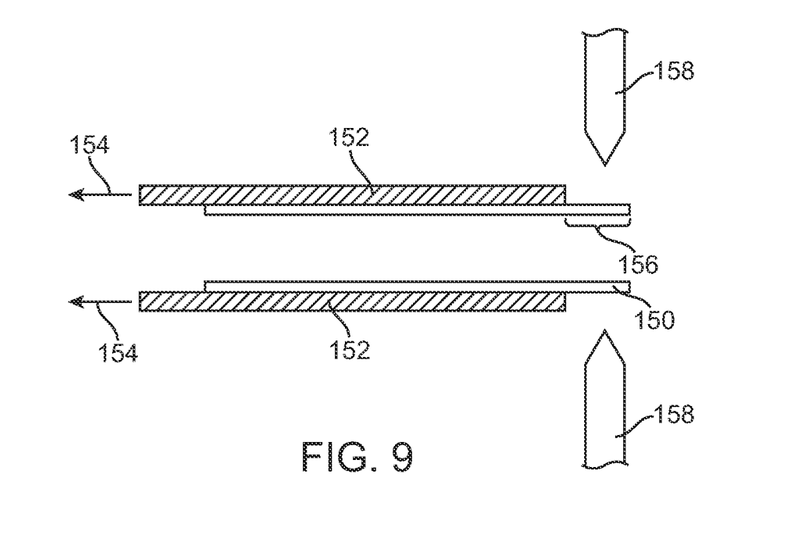
FIG. 9 depicts a stent having a sheath disposed over and retaining the stent at a reduced profile.

In additional embodiments, a method of forming connections between structural elements can include crimping a stent to a reduced profile followed by positioning a cylindrical sheath over the crimped stent to maintain the reduced profile. At least some structural elements of the stent in the reduced profile state are in contact or sufficiently close to form connections between them. The sheath may then be slid axially off of the stent to expose an axial section of the stent. Connections may then be formed on the exposed axial section. Connections may be formed in further axial sections of the stent in a step-wise fashion. FIG. 9 depicts a stent 150 having a sheath 152 disposed over and retaining stent 150 is a reduced profile or crimped configuration. Sheath 152 has been slid as shown by arrows 154 exposing axial section 156 of stent 150. Laser beam sources 158 are positioned to form connections between portions of structural elements in axial section 156. Sheath 152 is slid in a step-wise fashion in the direction of arrows 154 to exposed additional axial sections in which connections are formed.

In yet another embodiment, the full length of a polymer stent is crimped to a reduced profile. This brings structural elements into proximity which are to be joined to form breakable links. Next, all of the links are formed via application of heat to melt and fuse the elements together to form the links.

Generally, a stent may be formed, for example, from a tube or a sheet rolled into a tube. The sheet or tube, for example, may be formed by various methods known in the art such as extrusion or injection molding. A pattern may then be cut into the polymeric tube by laser cutting or chemical etching to form the stent.

Additionally, as mentioned above, a stent fabricated from embodiments of the stent described herein can be medicated with an active agent. A medicated stent may be fabricated by coating the surface of the polymeric scaffolding with a polymeric carrier that includes an active or bioactive agent or drug.

Embodiments of the present invention described herein may be applied to devices including, but not limited to, balloon expandable stents, self-expanding stents, and stent-grafts. In the case of a self-expanding stent, the stent can be crimped over a support, such as a catheter. The stent is used to open a lumen within an organ in a mammal, maintain lumen patency, or reduce the likelihood of narrowing of a lumen.

The method according to the invention can be used to increase retention in both polymeric and metallic stents. In one embodiment, the polymer for use in forming the stent scaffolding and/or the stent coating may be configured to degrade after implantation by fabricating the stent either partially or completely from biodegradable polymers.

In general, polymers for use in fabricating a substrate of a stent or a coating for a stent can be biostable, bioabsorbable, biodegradable or bioerodible. Biostable refers to polymers that are not biodegradable. The terms biodegradable, bioabsorbable, and bioerodible are used interchangeably and refer to polymers that are capable of being completely degraded and/or eroded when exposed to bodily fluids such as blood and can be gradually resorbed, absorbed, and/or eliminated by the body. The processes of breaking down and eventual absorption and elimination of the polymer can be caused by, for example, hydrolysis, metabolic processes, enzymolysis, oxidation, bulk or surface erosion, and the like.

It is understood that after the process of degradation, erosion, absorption, and/or resorption has been completed, no part of the stent will remain, or in the case of coating applications on a biostable scaffolding, no polymer will remain on the device. In some embodiments, very negligible traces or residue may be left behind. For stents made from a biodegradable polymer, the stent is intended to remain in the body for a duration of time until its intended function of, for example, maintaining vascular patency and/or drug delivery is accomplished.

Representative examples of polymers that may be used to fabricate or coat a stent include, but are not limited to, poly (N-acetylglucosamine) (Chitin), Chitosan, poly(hydroxyvalerate), poly(L-lactide) (PLLA), poly(L-lactide-co-D,L-lactide), poly(D,L-lactide), poly(D,L-lactide-co-glycolide), poly(glycolide), poly(L-lactide-co-glycolide) (PLGA), poly (hydroxybutyrate), poly(hydroxybutyrate-co-valerate), poly-orthoester, polyanhydride, poly(glycolic acid), poly(L-lactic acid), poly(D,L-lactic acid), poly(caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), poly(styrene-b-isobutylene-b-styrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Another type of polymer based on poly(lactic acid) that can be used includes graft copolymers, and block copolymers, such as AB block-copolymers ("diblock-copolymers") or ABA block-copolymers ("triblock-copolymers"), or mixtures thereof.

Additional representative examples of polymers that may be especially well suited for use in fabricating or coating a stent include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

The "glass transition temperature," Tg, is the temperature at which the amorphous domains of a polymer change from a brittle vitreous state to a solid deformable or ductile state at atmospheric pressure. In other words, the Tg corresponds to the temperature where the onset of segmental motion in the chains of the polymer occurs. When an amorphous or semi-crystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement. Tg of a given polymer can be dependent on the heating rate and can be influenced by the thermal history of the polymer. Furthermore, the chemical structure of the polymer heavily influences the glass transition by affecting chain mobility.

"Strength" refers to the maximum stress along an axis which a material will withstand prior to fracture. The ultimate strength is calculated from the maximum load applied during the test divided by the original cross-sectional area.

"Modulus" may be defined as the ratio of a component of stress or force per unit area applied to a material divided by the strain along an axis of applied force that results from the applied force. For example, a material has both a tensile and a compressive modulus. A material with a relatively high modulus tends to be stiff or rigid. Conversely, a material with a relatively low modulus tends to be flexible. The modulus of a material depends on the molecular composition and structure, temperature of the material, amount of deformation, and the strain rate or rate of deformation. For example, below its Tg, a polymer tends to be brittle with a high modulus. As the temperature of a polymer is increased from below to above its Tg, its modulus decreases.

"Strain" refers to the amount of elongation or compression that occurs in a material at a given stress or load.

"Elongation" may be defined as the increase in length in a material which occurs when subjected to stress. It is typically expressed as a percentage of the original length.

Example

Figure 10:
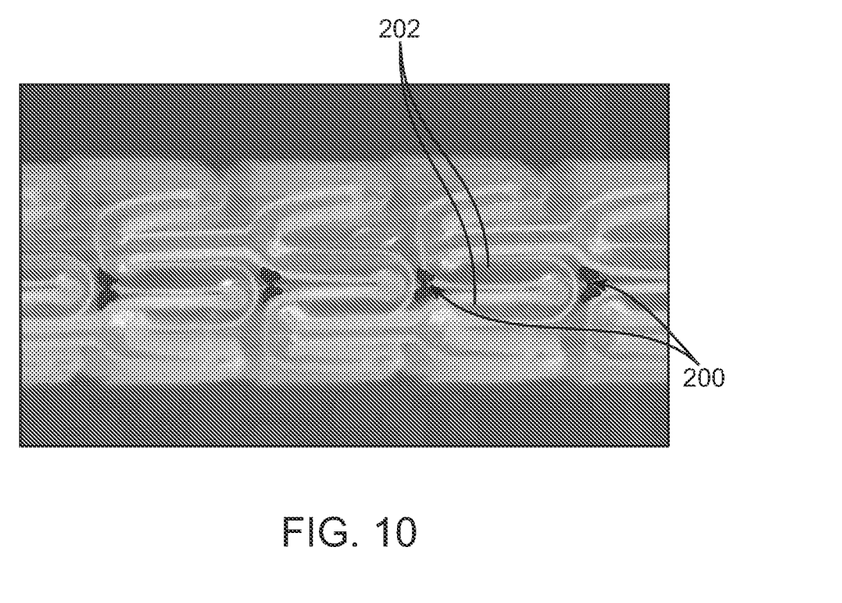
FIG. 10 depicts a stent formed from poly(L-lactide) having connecting elements or links formed between structural elements.

FIG. 10 depicts a stent formed from poly(L-lactide) having connecting elements or links 200 formed between structural elements 202.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of fabricating a stent comprising:
   crimping a polymer stent to a reduced profile onto a balloon catheter, wherein the stent is constructed of a pattern of a plurality of polymeric structural elements, wherein as the stent is crimped below the glass transition temperature of the structural elements, the structural elements plastically deform resulting in a gripping force on the balloon catheter by the crimped stent, wherein the gripping force retains the crimped stent on the balloon catheter at the reduced profile that is not sufficient to prevent the stent from shifting position or separating from the catheter prior to delivery; and followed by
   forming at least one breakable connecting element between two structural elements to facilitate retention of the stent at a reduced diameter so that the stent does not shift position or separate from the catheter prior to delivery, wherein upon expansion of the stent the at least one breakable connecting element breaks to allow expansion of the stent due to a radially outward force on the stent, wherein the forming comprises fusing the two structural elements together,
   wherein the connecting element is formed while the stent is crimped.

2. A method of fabricating a stent comprising:
   crimping a polymer stent to a reduced profile onto a balloon catheter, wherein the stent is constructed of a pattern of a plurality of polymeric structural elements, wherein the crimping occurs under the glass transition temperature of the structural elements and results in a gripping force by the crimped stent, wherein the gripping force retains the crimped stent on the balloon catheter at the reduced profile that is not sufficient to prevent the stent from shifting position or separating from the catheter prior to delivery; and followed by forming at least one breakable connecting element between two structural elements to facilitate retention of the stent at a reduced diameter of the reduced profile so that the stent does not shift position or separate from the catheter prior to delivery, wherein upon expansion of the stent the at least one breakable connecting element breaks to allow expansion of the stent due to a radially outward force on the stent, wherein the forming comprises fusing the two structural elements together.

* * * * *